(12) United States Patent
De Souza Ventura et al.

(10) Patent No.: US 8,883,740 B2
(45) Date of Patent: Nov. 11, 2014

(54) PEPTIDES, COMPOSITIONS, AND USES THEREOF

(75) Inventors: Janaina De Souza Ventura, Sao Paulo (BR); Linda Christian Carrijo Carvalho, Sao Paulo (BR); Ana Marisa Chudzinski-Tavassi, Sao Paulo (BR)

(73) Assignees: Ana Marisa Chudzinski-Tavassi, Sao Paulo (BR); Fundacao de Amparoa Pesquisa do Estado de Sao Paulo-Fapesp, Sao Paulo (BR); Biolab Sanus Farmaceutica Ltda., Taboao da Serra SP (BR)

( * ) Notice: Subject to any disclaimer, the term of this patent is extended or adjusted under 35 U.S.C. 154(b) by 157 days.

(21) Appl. No.: 12/863,922

(22) PCT Filed: Jan. 22, 2009

(86) PCT No.: PCT/IB2009/050237
§ 371 (c)(1),
(2), (4) Date: Oct. 18, 2010

(87) PCT Pub. No.: WO2009/093189
PCT Pub. Date: Jul. 30, 2009

(65) Prior Publication Data
US 2011/0034390 A1 Feb. 10, 2011

Related U.S. Application Data

(60) Provisional application No. 61/022,747, filed on Jan. 22, 2008.

(51) Int. Cl.
| A61K 38/48 | (2006.01) |
| C12N 9/50 | (2006.01) |
| A61K 38/08 | (2006.01) |
| A61K 38/10 | (2006.01) |
| A61K 38/18 | (2006.01) |
| C07K 7/00 | (2006.01) |
| C07K 14/475 | (2006.01) |
| C12N 9/64 | (2006.01) |
| A61K 38/00 | (2006.01) |

(52) U.S. Cl.
CPC .............. *C12N 9/6408* (2013.01); *A61K 38/00* (2013.01)
USPC ..... 514/21.6; 514/21.3; 514/21.4; 424/94.63; 530/327; 530/326; 530/324; 435/219

(58) Field of Classification Search
None
See application file for complete search history.

(56) References Cited

U.S. PATENT DOCUMENTS

| 7,049,096 B2 * | 5/2006 | Feder et al. .................. 435/69.1 |
| 2011/0214206 A1 * | 9/2011 | La Rosa et al. ............... 800/286 |

FOREIGN PATENT DOCUMENTS

| WO | WO 2006/021062 | 3/2006 |
| WO | WO 2007/028223 | * 3/2007 |

OTHER PUBLICATIONS

Reis et al., "Lopap, a prothrombin activator from *Lonomia* oblique belonging to the lipocalin family: recombinant production, biochemical characterization and structure-function insights," *Biochem. J.* 398:295-302, 2006.

* cited by examiner

*Primary Examiner* — Marianne P Allen
(74) *Attorney, Agent, or Firm* — Fish & Richardson P.C.

(57) ABSTRACT

Compositions for regenerating tissue and wound repair, among other applications, are described.

10 Claims, 5 Drawing Sheets

SEQUENCE LISTING

<160> NUMBER OF SEQ ID NOS: 7

<210> SEQ ID NO 1
<211> LENGTH: 11
<212> TYPE: PRT
<213> ORGANISM: Artificial Sequence
<220> FEATURE:
<223> OTHER INFORMATION: Synthetic

<400> SEQUENCE: 1

Tyr Ala Ile Gly Tyr Ser Cys Lys Asp Tyr Lys
1               5                   10

<210> SEQ ID NO 2
<211> LENGTH: 20
<212> TYPE: PRT
<213> ORGANISM: Artificial Sequence
<220> FEATURE:
<223> OTHER INFORMATION: Synthetic

<400> SEQUENCE: 2

Val Ser Lys Phe Asp Met Asn Ala Tyr Gln Gly Thr Trp Tyr Glu Ile
1               5                   10                  15

Lys Lys Phe Pro
            20

<210> SEQ ID NO 3
<211> LENGTH: 19
<212> TYPE: PRT
<213> ORGANISM: Artificial Sequence
<220> FEATURE:
<223> OTHER INFORMATION: Synthetic

<400> SEQUENCE: 3

Ala Pro Leu Trp Ile Leu Ser Thr Asp Tyr Asp Asn Tyr Ala Ile Gly
1               5                   10                  15

Tyr Ser Cys

<210> SEQ ID NO 4
<211> LENGTH: 19
<212> TYPE: PRT

```
<213> ORGANISM: Artificial Sequence
<220> FEATURE:
<223> OTHER INFORMATION: Synthetic

<400> SEQUENCE: 4

Ala Pro Leu Trp Ile Leu Ser Thr Asp Tyr Asp Asn Tyr Ala Ile Gly
 1               5                  10                  15

Tyr Ser Cys

<210> SEQ ID NO 5
<211> LENGTH: 23
<212> TYPE: PRT
<213> ORGANISM: Artificial Sequence
<220> FEATURE:
<223> OTHER INFORMATION: Synthetic

<400> SEQUENCE: 5

Ala Pro Leu Trp Ile Leu Ser Thr Asp Tyr Asp Asn Tyr Ala Ile Gly
 1               5                  10                  15

Tyr Ser Cys Lys Asp Tyr Lys
            20

<210> SEQ ID NO 6
<211> LENGTH: 7
<212> TYPE: PRT
<213> ORGANISM: Artificial Sequence
<220> FEATURE:
<223> OTHER INFORMATION: Synthetic

<400> SEQUENCE: 6

Tyr Ala Ile Gly Tyr Ser Cys
 1               5

<210> SEQ ID NO 7
<211> LENGTH: 69
<212> TYPE: DNA
<213> ORGANISM: Artificial Sequence
<220> FEATURE:
<223> OTHER INFORMATION: Synthetically Generated Oligonucleotide

<400> SEQUENCE: 7
gcaccgctgt ggattctttc tactgattac gacaactatg ctatcggcta ctcctgcaaa      60
gactacaag                                                              69
```

PEPTIDES, COMPOSITIONS, AND USES THEREOF

This application is a U.S. National Phase Application under 35 U.S.C. 371 of International Application PCT/IB2009/050237, filed on Jan. 22, 2009, which claims the benefit of the filing date of U.S. provisional application No. 61/022,747, which was filed on Jan. 22, 2008, the entire contents of each of which are hereby incorporated by reference in their entireties.

BACKGROUND OF THE INVENTION

The extracellular matrix (ECM) is a complex structural entity that surrounds and supports cells within living systems. In mammalian tissues the ECM is most commonly found in connective tissues such as tendon, cartilage, bone or dermis of the skin.

The ECM guides the generation of tissue and the repair of wounds, and several medical conditions are attributed to defectively-made ECM (e.g., scurvy); continually-degraded ECM (e.g., periodontal disease, non-healing ulcers); or deteriorating ECM or decreased ECM production (e.g., aged tissue). The importance of the ECM has prompted development of EMC-supplying therapies for use in tissue generation, wound repair, disease and aging treatments, and cosmetic uses.

SUMMARY OF THE INVENTION

The present invention features peptides capable of stimulating production of extracellular matrix (ECM) proteins in cells (e.g., fibroblasts), and hence can be utilized as a generating agent for tissue and skin as well as utilized as a cosmetic.

In some aspects, the disclosure provides an isolated peptide that includes the amino acid sequence YAIGYSC (SEQ ID NO:6). In some embodiments, the peptide stimulates production of ECM proteins (e.g., fibronectin, tenascin, collagen, procollagen, or a combination thereof).

In some aspects, the disclosure provides an isolated peptide that is substantially homologous or identical to SEQ ID NO:6.

In some aspects, the disclosure provides an isolated peptide that is substantially homologous to SEQ ID NO:1 or SEQ ID NO:3.

In another aspect, the disclosure provides a cosmetic composition that includes a peptide described herein (e.g., in combination with one or more cosmetically-acceptable excipients).

In another aspect, the disclosure provides a pharmaceutical composition that includes a peptide described herein (e.g., in combination with one or more pharmaceutically-acceptable excipients).

While the invention is described further below, we note here that the invention encompasses isolated peptides that consist of or that comprise an amino acid sequence that is at least 70% identical to (e.g., at least 75%, 80%, 85%, 90%, 95% or 100% identical) the amino acid sequence YAIGYSC (SEQ ID NO:6). The peptides can stimulate production of one or more extracellular matrix proteins in fibroblast cells (i.e., they are capable of stimulating production in vivo or in tissue culture). The isolated peptides can consist of or comprise an amino acid sequence that is at least 70% identical to (e.g., at least 75%, 80%, 85%, 90%, 95% or 100% identical to) the amino acid sequence YAIGYSCKDYK (SEQ ID NO:1). Such peptides can also stimulate production of one or more ECM proteins in cells (e.g., within fibroblast cells). The isolated peptides can consist of or comprise an amino acid sequence that is at least 70% identical to (e.g., at least 75%, 80%, 85%, 90%, 95% or 100% identical to) the amino acid sequence: APLWILSTDYDNYAIGYSC (SEQ ID NO:3). Such peptides can also stimulate production of one or more ECM proteins in cells (e.g., within fibroblast cells). The isolated peptides can consist of or comprise an amino acid sequence that is at least 70% identical to (e.g., at least 75%, 80%, 85%, 90%, 95% or 100% identical to) the amino acid sequence APLWILSTDYDNYAIGYSCKDYK (SEQ ID NO:5). Such peptides can also stimulate production of one or more ECM proteins in cells (e.g., within fibroblast cells.

The isolated peptide can consist of or comprise an amino acid sequence that differs from a reference sequence (e.g., SEQ ID NO:6, SEQ ID NO:1, SEQ ID NO:3, or SEQ ID NO:5) by virtue of including one or more amino acid substitutions, additions, or deletions. For example, the isolated peptide can differ from a peptide represented by SEQ ID NO:6 by up to four amino acid substitutions, additions, and/or deletions. The peptides that differ from a reference sequence can be capable of stimulating production of one or more ECM proteins in fibroblast cells. Other isolated peptides can differ from SEQ ID NO:1 by up to six amino acid substitutions, additions, and/or deletions and be capable of stimulating production of one or more ECM proteins in fibroblast cells. Other isolated peptide can differ from SEQ ID NO:5 by up to twelve amino acid substitutions, additions, and/or deletions and be capable of stimulating production of one or more extracellular matrix proteins in fibroblast cells.

The invention further encompasses pharmaceutical compositions that include a peptide described herein (e.g., a peptide that consists of or comprises an amino acid sequence that is at least 70% identical to the amino acid sequence YAIGYSC (SEQ ID NO:6). The pharmaceutical composition can include a pharmaceutically acceptable carrier (e.g., a water-based diluent) and can be in the form of a liquid or an ointment. The pharmaceutical compositions can further include a wound healing agent. The pharmaceutical composition can be formulated for oral, intramuscular, intravenous, subcutaneous, topical, pulmonary, intranasal, buccal, rectal, sublingual, intradermal, intraperitoneal or intrathecal use.

The methods of the invention encompass methods of reducing cell death and/or tissue degeneration in a subject by administering one or more of the pharmaceutical compositions described herein to the cells of the subject (e.g., a human patient). The subject may have been identified as experiencing cell death and/or tissue generation caused, for example, by disease, trauma, or aging. The methods can further include administering a wound healing agent.

The methods of the invention encompass methods of wound healing and/or regenerating tissue in a subject by administering one or more of the pharmaceutical compositions described herein to the subject (e.g., a human patient). The methods can further include a step of identifying a patient in need of treatment and, optionally, further administering a wound healing agent.

Any of the compositions can be administered in a therapeutically effective amount.

Also within the scope of the present invention is the use of an isolated peptide as described herein in the preparation of a medicament. The medicament can be for reducing cell death and/or tissue degeneration or for wound healing and/or regenerating tissue.

DETAILED DESCRIPTION OF THE INVENTION

Figure 1:
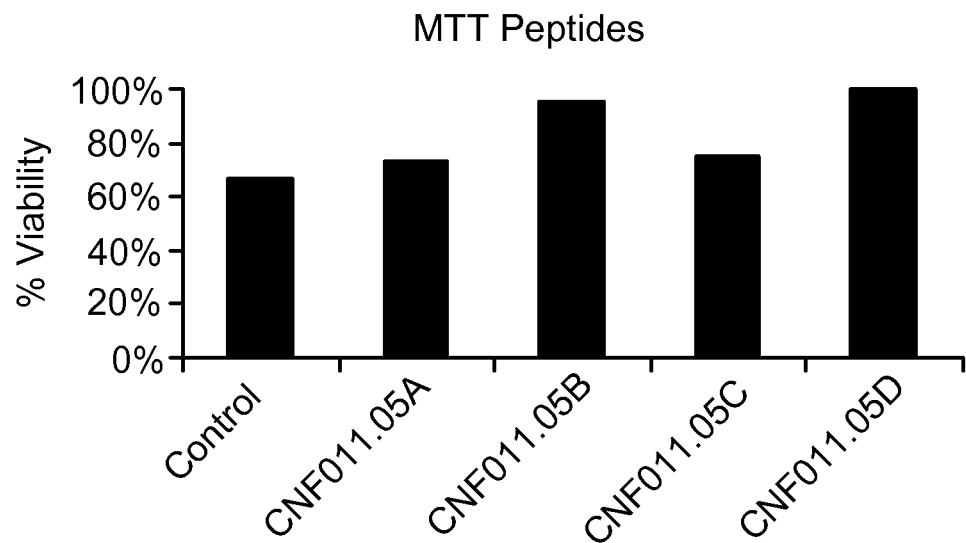
FIG. 1 is a bar graph showing the influence of four peptides on the viability of cells tested by MTT (3-[4,5-dimethylthiazol-2-yl]-2,5-diphenyltetrazolium bromide).

The present disclosure features novel peptides that are useful for stimulating production of ECM proteins, particularly fibronectin, tenascin, collagen, and procollagen. Described herein are methods of using such peptides, methods of making such peptides, and kits and compositions containing such peptides.

The peptides may be used to generate extracellular matrix proteins, particularly fibronectin, tenascin, collagen, and procollagen. The peptides may be used for a variety of beneficial purposes, such as the generation of tissue that has been diseased, damaged, or lost (e.g., due to wounds, trauma, surgical procedures or tissue implants, bone disease, cosmetic defects, cartilage disease, periodontal disease, photo or chrono aging, dermal wounds caused by circulatory disorders, diabetes, infectious diseases, and the like). The peptides may be used for the prevention of tissue degeneration (e.g., failing tissue structure or tissue loss) due to tissue disease, trauma, or aging. The peptides may be used for wound repair. The peptides can be used for wound repair with reduced scarring (e.g., reduced amounts of scar tissue or dense fibrous connective tissue after healing in comparison to nontreatment). They also can be used in different diseases involving dysfunction of collagen or ECM components (e.g., asthma).

The description of the uses and the embodiments of the invention are illustrative only and not intended to be limiting.
Definitions "Extracellular Matrix" or ECM is a complex structural entity that surrounds and supports cells within living systems. In mammalian tissues, the ECM is most commonly found in connective tissues such as tendon, cartilage, bone and the dermis of the skin. The ECM is produced and maintained by the cells that inhabit it.

"Extracellular Matrix Proteins" or ECM proteins are one or more of fibronectin, laminin, vitronectin, tenascin, entactin, thrombospondin, elastin, gelatin, a collagen, fibrillin, merosin, anchorin, chondronectin, link protein, bone sialoprotein, osteocalcin, osteopontin, epinectin, hyaluronectin, undulin, epiligrin, and kalinin. The term encompasses presently unknown extracellular matrix proteins that may be discovered in the future, since their characterization as an extracellular matrix protein will be determinable by one of ordinary skill in the art.

"Substantially Homologous" refers to peptides that include an amino acid sequence that is at least 70% (e.g., 70%, 75%, 80%, 82%, 85%, 86%, 87%, 88%, 89%, 90%, 91%, 92%, 93%, 94%, 95%, 96%, 97%, 98%, 99%) identical to an amino acid sequence (for example, the amino acid sequence represented by SEQ ID NO:1) when compared or aligned for maximum correspondence through the use of sequence comparison algorithms, as, for example, the BLAST algorithm, (Altschul et al., *JMB* 215:403-410 (1990)), the homology algorithm of Smith & Waterman (*Adv. Appl. Math.* 2:482 (1981)), the homology algorithm of Needleman & Wunsch (*JMB* 48:443 (1970)), and the similarity search method of Pearson & Lipman (*PNAS USA* 85:2444 (1988)). Several computer programs can implement these algorithms (e.g., GAP, BESTFIT, FASTA, and TFASTA (Wisconsin Genetics Computer Group, USA).

Trauma

Tissues can sustain a variety of injuries, including penetrating trauma, burn trauma and blunt trauma. All of these insults set into motion an orderly sequence of events that are involved in the healing response, characterized by the movement of specialized cells into the wound site. If the tissue has been disrupted, the specialized cells deposit extracellular matrix proteins (e.g., collagen) into the wound site, which is needed to repair the defect and restore anatomic structure and function. If too little extracellular matrix proteins deposited, the wound is weak and may dehisce.

Healing and the Healing Cascade consists of three phases: an inflammatory phase, a proliferative phase, and a remodeling phase. The inflammatory phase is initiated by collagen exposed during wound formation, which activates blood clotting proteins. Shortly thereafter, inflammatory cells migrate to the wound. Platelets, the first response cells, release several proteins including fibronectin, which control bleeding and chemoattract other cells. Neutrophils, the second response cells, kill bacteria and remove foreign debris. Leukocytes and macophages, the later response cells, release several proteins, including collagenases, which debride the wound, and cytokines, which stimulate collagen production and angiogenesis by fibroblasts.

The proliferative phase comprises epithelialization, angiogenesis, granulation tissue formation, and collagen deposition. In epithelialization, if the basement membrane is intact (as in first-degree burns), epithelial cells migrate normally into the wound. If it been destroyed (as in second- and third-degree burns), epithelial cells from the periphery reepithelialize the wound. In angiogenesis, endothelial cells migrate to the wound and capillaries are formed. In granulation tissue formation and collagen deposition, fibroblasts differentiate and deposit ground substance (e.g., extracellular matrix proteins (e.g., procollagen)) into the wound.

The maturational phase is marked by cross-linking and organization (e.g., specific enzymatic degradation of collagen) of the new extracellular matrix.

Treatments of wounds are classified into two major categories: (1) Primary Intention: involves physical closure of the wound, usually by sutures, tape, staples, bandages, and the like. The main mechanism of healing during Primary Intention is connective tissue matrix deposition, where collagen, proteoglycans and attachment proteins are deposited to form a new extracellular matrix; and (2) Secondary Intention:

leaves the wound open, and it heals by contraction; the interaction between cells and matrix results in movement of cells and tissue toward the center of the wound.

Examples of tissues that can be regenerated and repaired using the peptides described herein include nervous tissue, skin, vascular tissue, cardiac tissue, pericardial tissue, muscle tissue, ocular tissue, periodontal tissue, connective tissue such as bone, cartilage, tendon, and ligament, organ tissue such as kidney tissue, and liver tissue, glandular tissue such as pancreatic tissue, mammary tissue, and adrenal tissue, urological tissue such as bladder tissue and ureter tissue, and digestive tissue such as intestinal tissues.

Aging

Aged tissue, for example, skin, is marked by deteriorating ECM or decreased production of ECM, and a deterioration of the foundation of the ECM. These properties lead to failing tissue structure. Aged tissue is weaker and less elastic and flexible than younger skin. It loses stamina, and aged skin undergoes rippling (e.g., wrinkling).

Treatments of wrinkles (and scars) have principally involved injecting filler into the dermal layer of skin proximate to the defect or desired area of tissue. Examples of fillers include mineral oil, fat, bovine collagen, and human collagen. All fillers have well-documented limitations. For example, human collagen is partly effective in reducing wrinkles, but requires repeated painful injections with large needles to compensate for collagen absorption by the body.

Peptides

The present invention describes peptides capable of stimulating production of extracellular matrix (ECM) proteins (e.g., fibronectin, tenascin, collagen, and procollagen), and hence can be utilized as an agent that generates or facilitates the generation of tissue or skin, and as a wound repair agent.

The peptides of the present invention include peptides that consist of or include the sequence YAIGYSC (SEQ ID NO:6), YAIGYSCKDYK (SEQ ID NO:1), APLWILSTDYDNYAI-GYSC (SEQ ID NO:3), or APLWILSTDYDNYAIGYSCK-DYK (SEQ ID NO:5). A peptide consisting of SEQ ID NO:1 is referred to herein as "the CNF011.05D peptide."

Also included are peptides that are substantially homologous to SEQ ID NO:6; and peptides encoded by a nucleic acid that hybridizes under high stringency conditions to a peptide of SEQ ID NO:6.

Also included are peptides that are substantially homologous to SEQ ID NO:1; and peptides encoded by a nucleic acid that hybridizes under high stringency conditions to a peptide of SEQ ID NO:1.

Also included are peptides that are substantially homologous to SEQ ID NO:3; and peptides encoded by a nucleic acid that hybridizes under high stringency conditions to a peptide of SEQ ID NO:3.

As used herein, the term "hybridizes under high stringency conditions" describes conditions for hybridization and washing. Guidance for performing hybridization reactions can be found in Current Protocols in Molecular Biology, John Wiley & Sons, N.Y. (1989), 6.3.1-6.3.6, which is incorporated by reference. High stringency hybridization conditions include hybridization in 6×SSC at about 45° C., followed by one or more washes in 0.2×SSC, 0.1% SDS at 65° C., or substantially similar conditions.

Also included are peptides that contain, consist essentially of, or consist of an amino acid sequence that differs from the sequence of SEQ ID NO:5 by one, two, three, four, five, six, seven, eight, nine, ten, eleven, twelve, thirteen, fourteen, fifteen, sixteen, seventeen, eighteen, nineteen, twenty, twenty-one, or twenty-two acid substitutions, additions, or deletions. They can be at any position, e.g., internal or terminal (e.g., at the N or C terminus).

The N- and/or C-terminus of the peptide can be modified to increase stability, e.g., to decrease degradation, e.g., proteolytic degradation.

The peptides can be modified to contain an epitope tag (e.g., a His (e.g., 6×His or poly-His), Myc, HA, GST, MBP, VSV, Thioredoxin, Beta-galactosidase, FLAG, fluorescent protein (e.g., GFP) tag, or the like) for example, to aid in the identification or purification of the peptide. A cleavage site (e.g., a recognition site for Factor Xa Protease, enterokinase, thrombin, TEV protease, PRESCISSION™ protease, intein 1 or intein 2, or a signal peptidase, etc.) can optionally be situated between the tag and peptide sequence so that the tag can be cleaved from the peptide. Such techniques are known in the art. See also Current Protocols in Molecular Biology, John Wiley and Sons, Inc, New York, N.Y.

Peptide Preparation

The peptides described herein can be prepared in a biological system or chemically synthesized.

To produce the peptides in a biological system, the peptide can be produced by recombinant DNA technology. For example, an expression vector containing a nucleic acid sequence encoding a peptide described herein (e.g., the peptide represented by SEQ ID NO:5 can be encoded by nucleic acid sequence gca-ccg-ctg-tgg-att-ctt-tct-act-gat-tac-gac-aac-tat-gct-atc-ggc-tac-tcc-tgc-aaa-gac-tac-aag (SEQ ID NO:7) or a related sequence according to the genetic code; and peptides represented by SEQ ID NO:6, SEQ ID NO:1, and SEQ ID NO:3, can be encoded by nucleic acid sequences derived from SEQ ID NO:7 or related sequences according to the genetic code) can be introduced into a biological system (e.g., a bacterial, yeast, plant, insect, or mammalian expression system) and expressed using standard techniques. The peptide is then purified from the biological system (e.g., from cells or culture medium) using standard purification techniques (e.g., using separation techniques based on the physical or chemical properties of the peptide or affinity purification techniques). Such techniques are known in the art. See, e.g., Current Protocols in Molecular Biology 3rd ed., John Wiley and Sons, Inc, New York, N.Y.

The peptides can be chemically synthesized, e.g., using liquid or solid phase synthesis. Such techniques are standard in the art, see, e.g., Atherton, E., Sheppard, R. C. Solid Phase peptide synthesis: A practical approach. IRL Press, Oxford, England, 1989; Stewart J. M., Young, J. D. Solid phase peptide synthesis, 2nd edition, Pierce Chemical Company, Rockford, 1984; Carpino (J. Am. Chem. Soc. 115:4397-4398 (1992)). Peptides are synthesized by coupling the carboxyl group or C-terminus of one amino acid to the amino group or N-terminus of another.

Cosmetic Compositions

A peptide of the disclosure can be formulated as a cosmetic composition, e.g., for administration to a subject to treat skin. The peptide can be administered alone or in combination with another cosmetic, either in the same composition or as a separate composition.

Typically, a cosmetic composition includes a cosmetically acceptable carrier. As used herein, "cosmetically acceptable carrier" includes any and all solid, semi-solid and liquid thickeners; excipients, diluents; substances with UV filtration properties; perfumes; cosmetic bases; and cosmetic formulations.

The cosmetic composition may be in a variety of forms. These include, for example, liquid, semi-solid and solid dosage forms, such as liquid solutions, powders, pomades, gels, cremes, adhesives, etc.

Pharmaceutical Compositions

A peptide of the disclosure can be formulated as a pharmaceutical composition, e.g., for administration to a subject to generate tissue or repair skin. The peptide can be administered alone or in combination with another pharmaceutical, either in the same composition or as a separate composition.

Typically, a pharmaceutical composition includes a pharmaceutically acceptable carrier. As used herein, "pharmaceutically acceptable carrier" includes any and all solvents, excipients, dispersion media, coatings, antibacterial and antifungal agents, isotonic and absorption delaying agents, liposomes, microparticles, microspheres, nanospheres, and the like that are physiologically compatible.

The pharmaceutical composition can include a pharmaceutically acceptable salt of the peptide, e.g., an acid addition salt or a base addition salt (see e.g., Berge et al. *J. Pharm. Sci.* 66:1-19 (1977)).

Pharmaceutical formulation is a well-established art, and is further described, e.g., in Gennaro (ed.), Remington: The Science and Practice of Pharmacy, 20th ed., Lippincott, Williams & Wilkins (2000) (ISBN: 0683306472); Ansel et al., Pharmaceutical Dosage Forms and Drug Delivery Systems, 7th Ed., Lippincott Williams & Wilkins Publishers (1999) (ISBN: 0683305727); and Kibbe (ed.), Handbook of Pharmaceutical Excipients American Pharmaceutical Association, 3rd ed. (2000) (ISBN: 091733096X).

In one embodiment, the excipients include saline, sodium chloride, sodium dibasic phosphate heptahydrate, sodium monobasic phosphate, and stabilizers.

The pharmaceutical compositions may be in a variety of forms. These include, for example, liquid, semi-solid and solid dosage forms, such as liquid solutions (e.g., injectable and infusible solutions), dispersions or suspensions, tablets, pills, powders, suppositories, gels, or ointments. The preferred form can depend on the intended mode of administration and therapeutic application.

The pharmaceutical compositions can be formulated for topical administration, e.g., at a site of a wound. Topical administration includes, for example, epicutaneous, intranasal, inhalational, and vaginal administration. The composition can be administered to skin (e.g., for a burn, blister, or cut), lip, gum, tooth, oral cavity, eye, ear, nail bed, or throat, etc., e.g., at the site of a wound. The composition for topical administration can be in a cream, gel, lotion, or salve, etc.

In certain embodiments, the pharmaceutically acceptable carrier can protect the peptide against rapid release or degradation (e.g., to prepare a controlled release formulation), including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known, e.g., Sustained and Controlled Release Drug Delivery Systems, J. R. Robinson, ed., Marcel Dekker, Inc., New York, 1978.

In certain embodiments, the pharmaceutical composition may be prepared with a wound healing agent. As used herein, "wound healing agent" includes any and all agents that promote wound repair, tissue generation, or prevent or inhibit tissue degeneration. Examples of wound healing agents include agents that stimulate production of extracellular matrix (ECM) proteins, structural elements of the ECM (e.g., proteins, glycoproteins, proteoglycans and glycosaminoglycans), growth factors and differentiating factors (see Adams et al., *Development* 117:1183-1198 (1993) and Kreis et al. (eds.), "Guidebook to the Extracellular Matrix and Adhesion Proteins," Oxford University Press (1993) (hereinafter "Kreis et al."), and scaffolding materials (e.g., US Application No. 20030211793). The teachings of Adams et al. and Kreis et al. are incorporated herein by reference, which describe growth factors and ECM components that regulate differentiation and development.

Examples of growth factors and differentiation factors include, but are not limited to, epidermal growth factor, fibroblast growth factor, insulin growth factor, nerve growth-factor, mast cell-stimulating factor, platelet-derived growth factor, transforming growth factor-d, platelet-derived growth factor, scatter factor, hepatocyte growth factor and Schwann cell growth factor.

When the peptide is used in combination with a wound healing agent, the two agents can be formulated separately or together.

Administration

The peptide can be administered to a subject, e.g., a human subject, by a variety of methods. For many applications, the route of administration is parenteral, e.g., one of: intravenous injection or infusion (IV), intraarterial injection, subcutaneous injection (SC), intraperitoneally (IP), intracardiac injection, intraosseous infusion, intradermal injection, intraperitoneal infusion or injection, intravitreal injection, intramuscular injection, intrathecal injection, intra-articular injection, or epidural administration. In some preferred embodiments, the peptide is administered by an enteral route (e.g., orally). The peptide can be administered locally, e.g., topically (e.g., epicutaneously, intranasally, inhalationally, vaginally, etc.) (e.g., in a cream, gel, lotion, or salve), e.g., to the skin or lip or gum or oral cavity or throat, e.g., at the site of a wound. In some cases, administration may be directly to the site needing extracellular matrix.

The peptide can be administered locally or systemically.

The peptide can be administered e.g., by injection, infusion, diffusion, implants, topical application, or oral delivery.

The peptide can be administered as a fixed dose, or in a µg/kg or mg/kg dose.

The dose can also be chosen to reduce or avoid production of antibodies against the peptide.

The route and/or mode of administration of the peptide can also be tailored for the individual case, e.g., by evaluating or monitoring the subject, e.g., using electromyography, nerve conduction studies, evoked potential studies, magnetic resonance imaging, neurological examination, X-rays, and/or standard parameters associated with the particular disorder, e.g., criteria for assessing back pain.

Dosage regimens are adjusted to provide the desired response, e.g., a therapeutic response or a combinatorial therapeutic effect. Generally, any combination of doses (either separate or co-formulated) of the peptide (and optionally a second agent, e.g., as described herein) can be used in order to provide a subject with the peptide in bioavailable quantities. For example, doses in the range of 0.1 µg/kg-10 mg/kg, 1 µg/kg-1 mg/kg, 1 µg/kg-100 µg/kg, 5 µg/kg-500 µg/kg, 0.1-100 mg/kg, 0.5-100 mg/kg, 1 mg/kg-100 mg/kg, 0.5-20 mg/kg, or 1-10 mg/kg can be administered. Other doses can also be used.

Dosage unit form or "fixed dose" as used herein refers to physically discrete units suited as unitary dosages for the subjects to be treated; each unit contains a predetermined quantity of active compound calculated to produce the desired therapeutic effect in association with the required pharmaceutical carrier and optionally in association with the other agent. Single or multiple dosages may be given. Alternatively, or in addition, the peptide may be administered via continuous infusion.

The peptide can be administered, e.g., once or twice daily, or about one to four times per week, or preferably weekly, biweekly, or monthly, e.g., for between about 1 to 10 weeks, or longer if needed for a subject undergoing a long course of treatment. The skilled artisan will appreciate that certain factors may influence the dosage and timing required to effectively treat a subject, including but not limited to the severity of the disease or disorder, formulation, route of delivery, previous treatments, the general health and/or age of the subject, other diseases present, and other treatments a subject has undergone. Moreover, treatment of a subject with a therapeutically effective amount of a peptide can include a single treatment or, preferably, can include a series of treatments. Animal models can also be used to determine a useful dose, e.g., an initial dose or a regimen. For example, animal studies can be used to measure how long the extracellular matrix promoted by the peptide lasts.

If a subject is at risk for tissue degeneration (e.g., failing tissue structure aging or tissue loss) due to tissue damage, disease, or trauma, the peptide can be administered before or during the event that may cause tissue degeneration, e.g., as a preventative measure. The duration of such preventative treatment can be a single dosage of the peptide or the treatment may continue (e.g., multiple dosages) from a time before the event, during the event, and/or after the event, e.g., to minimize loss in the subject. For example, a subject at risk of tissue loss may be treated with the peptide for hours or days before the event that may cause tissue degeneration, so as to prevent tissue loss from occurring or to decrease the amount of tissue loss experienced.

A pharmaceutical composition may include a "therapeutically effective amount" of a peptide described herein. Such effective amounts can be determined based on the effect of the administered agent (e.g., peptide), or the combinatorial effect of agents if more than one agent is used. A therapeutically effective amount of an agent may also vary according to factors such as the type of pain, disease state, age, sex, and weight of the subject, and the ability of the agent to elicit a desired response in the subject, e.g., wound repair. A therapeutically effective amount is also one in which any toxic or detrimental effects of the composition are outweighed by the therapeutically beneficial effects.

As used herein, the "subject" can be any organism in need of repair, reconstruction, or replacement of an extracellular matrix to generate or repair tissue that has been damaged, diseased, or lost, e.g., a mammal, e.g., human, farm animal (e.g., horse, donkey, mule, cattle, cow, bull, sheep, pig, etc.), domestic pet (e.g., dog, cat, rat, mouse, rabbit, hamster, guinea pig, ferret, etc.), or zoo animal (e.g., giraffe, lion, tiger, bear, zebra, monkey, gorilla, whale, dolphin, etc.).

In Vitro Use

The peptides may be used in vitro, for example, as model systems for research, or to make prostheses or implants to replace damaged or diseased tissues, or to provide scaffolds which, when occupied by cells, e.g., host cells, are remodeled to become functional tissues Devices and Kits Pharmaceutical compositions that include the peptide can be administered with a medical device. The device can include, e.g., one or more housings for storing pharmaceutical preparations that include the peptide, and can be configured to deliver one or more unit doses of the peptide. The device can be further configured to administer a second agent, e.g., a tissue generation or wound repair agent described herein, either as a single pharmaceutical composition that also includes the peptide or as two separate pharmaceutical compositions.

For example, the pharmaceutical composition can be administered with a needleless hypodermic injection device (e.g., U.S. Pat. Nos. 5,399,163; 5,383,851; 5,312,335; 5,064,413; 4,941,880; 4,790,824; or U.S. Pat. No. 4,596,556); by implant, module, or pump (e.g., U.S. Pat. Nos. 4,487,603; 4,447,233; 4,447,224); by skin administrating devices (e.g., U.S. Pat. No. 4,486,194), and by osmostic drug delivery systems (e.g., U.S. Pat. No. 4,439,196). Many other devices, implants, delivery systems, and modules are also known.

A peptide can be provided in a kit. In one embodiment, the kit includes (a) a container that contains a composition that includes a peptide described herein, and optionally (b) informational material. The informational material can be descriptive, instructional, marketing or other material that relates to the methods described herein and/or the use of the peptide for therapeutic benefit.

In an embodiment, the kit also includes a second agent for tissue generation or wound repair, e.g., another agent described herein. For example, the kit includes a first container that contains a composition that includes the peptide, a second container that includes the second agent, and optionally informational material.

In addition to the peptide, the composition in the kit can include other ingredients, such as a solvent or buffer, a stabilizer, or a preservative. The peptide can be provided in any form, e.g., liquid, dried or lyophilized form, preferably substantially pure and/or sterile. When the agents are provided as a dried form, reconstitution generally is by the addition of a suitable solvent. The solvent, e.g., sterile water or buffer, can optionally be provided in the kit.

The kit optionally includes a device suitable for administration of the composition, e.g., a syringe or other suitable delivery device. The device can be provided pre-loaded with one or both of the agents or can be empty, but suitable for loading.

EXAMPLES

The illustrative examples of the present invention utilized the synthetic peptides presented in Table 1, and were synthesized by ORPEGEN Pharma (Germany).

TABLE 1

| Peptide | Molecular Mass | Sequence | | |
|---|---|---|---|---|
| CNF011.05A | 2452.8 | VSKFDMNAYQGTWYEIK KFP | SEQ ID NO: | 2 |
| CNF011.05B | 2165.4 | APLWILSTDYDNYAIGY SC | SEQ ID NO: | 3 |
| CNF011.05C | 2305.7 | IWILSRTKTLNESSKST VNK | SEQ ID NO: | 4 |
| CNF011.05D | 1310.5 | YAIGYSCKDYK | SEQ ID NO: | 1 |

Example 1

Effect on Cell Viability

Tests for cell viability (% viability) was realized utilizing reduced serum conditions and MTT (3-[4,5-Dimethylthiazol-2-yl]-2,5-Diphenyltetrazolium bromide) colorometric assay (Mosmann, 1983). The results are illustrated in FIGS. 1 to 3.

FIG. 1 illustrates the effect of peptides (5 μg/ml) on cell viability (% viability) of endothelial cells (HUVEC) when incubated together for 48 hours in RPMI 1640 with 1% FBS. The control has cells incubated in RPMI 1640 with 1% FBS (with no peptide).

Figure 2:
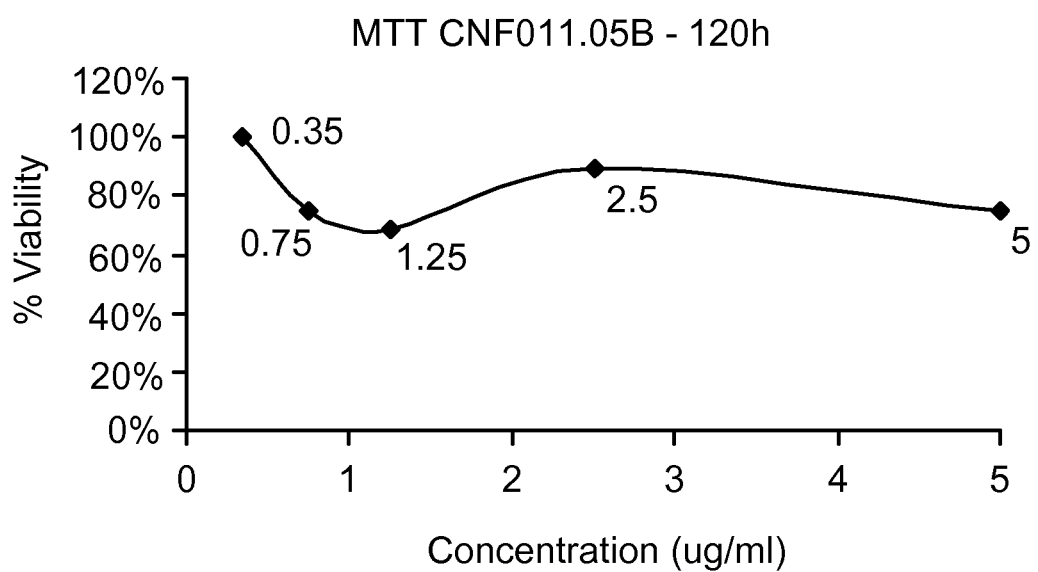
FIG. 2 is a line graph showing the influence of peptide CNF011.05B on the viability, tested by MTT, of endothelial cells incubated for 120 hours in medium supplemented with 1% FBS.

FIG. 2 illustrates the effect of different concentrations of CNF011.05B on cell viability (% viability) of endothelial cells when incubated together for 120 hours in RPMI supplemented with 1% FBS.

Figure 3:
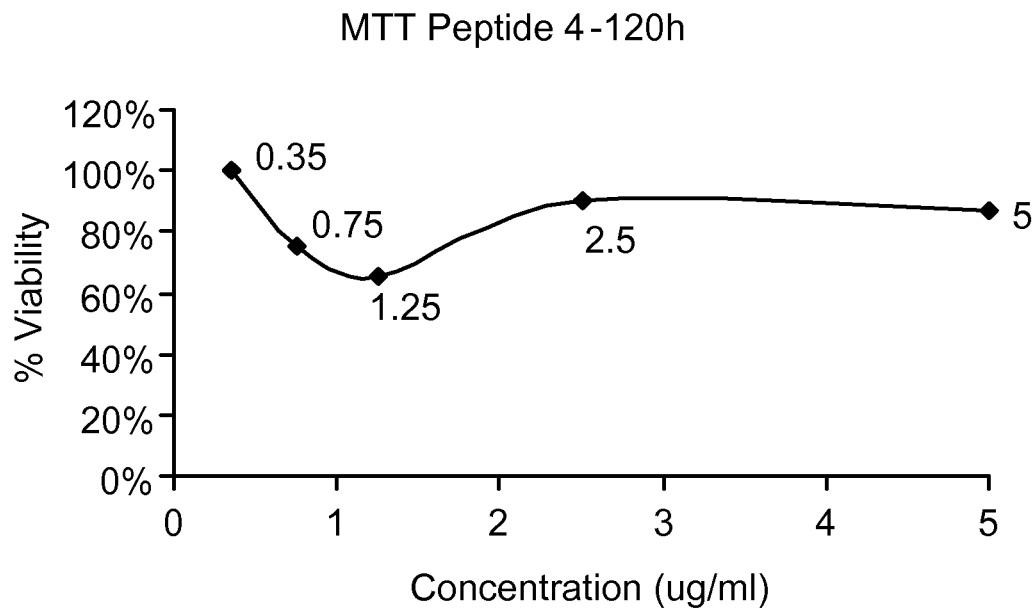
FIG. 3 is a line graph showing the influence of peptide CNF011.05D on the viability, tested by MTT, of endothelial cells incubated for 120 hours in medium supplemented with 1% FBS.

FIG. 3 illustrates the effect of different concentrations of CNF011.05D on cell viability (% viability) of endothelial cells when incubated together for 48 hours in RPMI supplemented with 1% FBS.

The results demonstrate that peptides CNF011.05B and CNF011.05D (5 µg/ml) augment cell viability under apoptotic conditions induced by the deprivation of fetal bovine serum (FBS), probably through a mechanism of inhibiting programmed cell death and apoptosis.

The augmentation in cell viability supports the use of CNF011.05B and CNF011.05D in wound repair, for such augmentation can increase (1) cell viability in wounds and (2) prevent matrix loss in wounds (Gilbert et. al., *Tissue Eng.*, 2009, January 2, electronic PubMed submission). Such augmentation in cell viability also supports the use of these peptides in tissue generation and prevention of tissue degeneration.

Example 2

Production of Nitric Oxide (NO)

Figure 4:
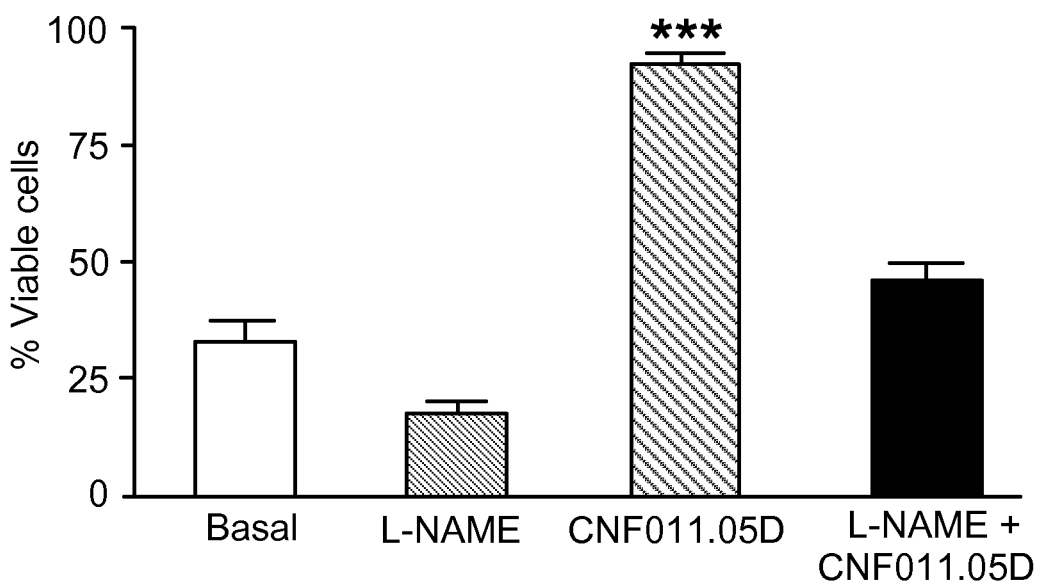
FIG. 4 is a bar graph showing the influence of peptide CNF011.05D plus L-NAME on the viability, tested by flow cytometry, of neutrophils incubated in medium supplemented with 1% FBS.
Figure 5:
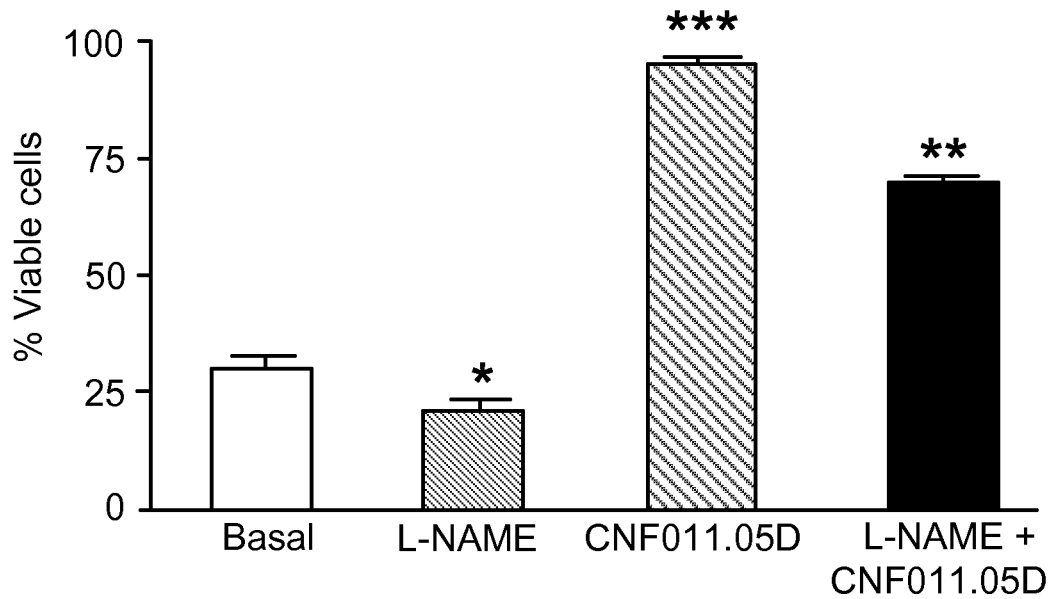
FIG. 5 is a bar graph showing the influence of peptide CNF011.05D plus L-NAME on the viability, tested by flow cytometry, of primary endothelial cells incubated in medium supplemented with 1% FBS.
Figure 6:
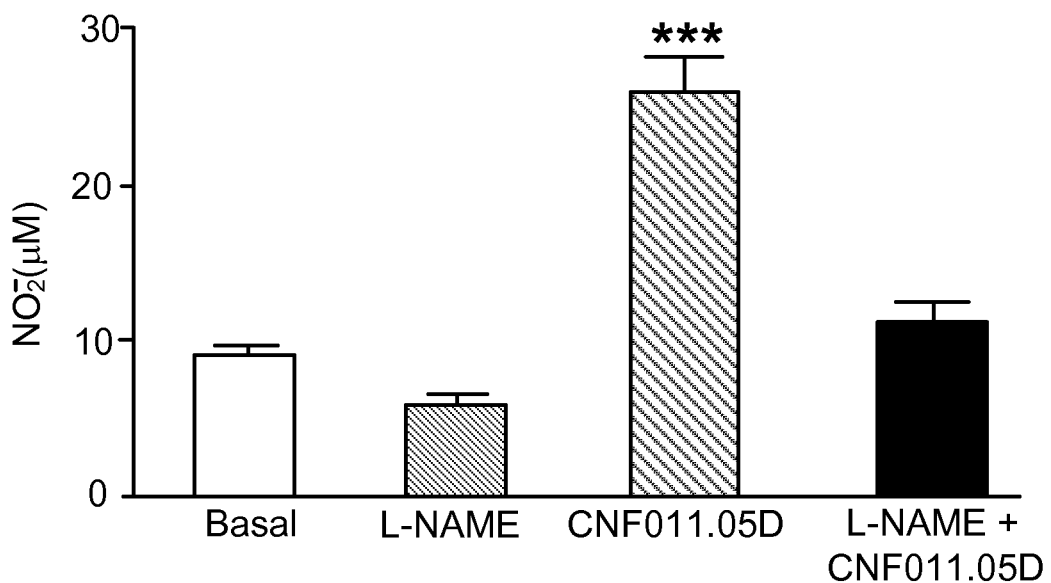
FIG. 6 is a bar graph showing the influence of peptide CNF011.05D plus L-NAME on $NO_2$ production by neurophils as measured by use of the Griess reaction.

Neutrophils or primary cultured endothelial cells from Wistar Rats were cultured in reduced serum medium (1%) in presence of CNF011.05D (3.0 µm/mL) and/or 1M L-NAME, an inhibitor of NO synthase (and accordingly, an inhibitor of NO and resulting metabolite $NO_2$ production). After 24 hours, cell viability was measured using flow cytometry analysis with FITC annexin V (1:500) and propidium iodide (10 µl of 50 mg/ml). The viability of both neutrophils (FIG. 4) and primary endothelial cells (FIG. 5) was increased with the peptide CNF011.05D alone, and this increase was diminished in presence of L-NAME.

Measurement of Nitric Oxide (NO)

Figure 9:
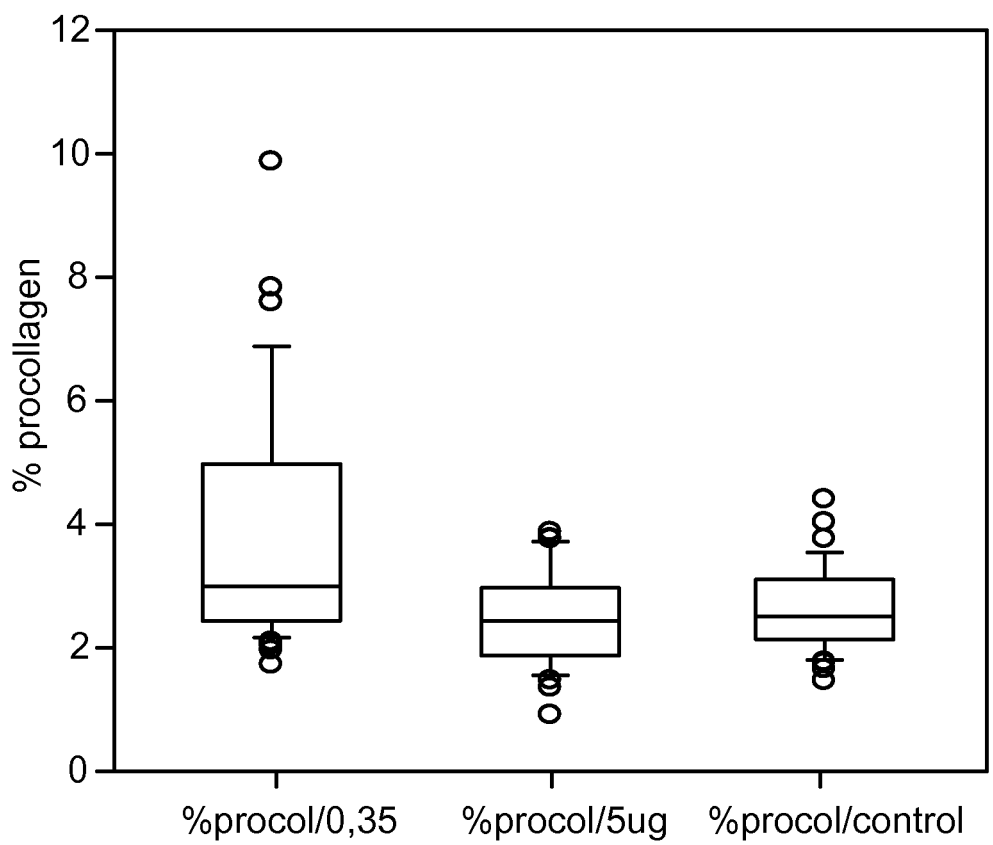
FIG. 9 is a plot illustrating the percent of fibroblasts producing procollagen upon incubation with peptide CNF011.05D at 0.35 µg and 5 µg.

Neutrophils were cultured for 18 hours with CNF011.05D (1.5 µg/ml), and production of NO metabolite $NO_2$ secreted into culture was assessed by use of the Griess reaction, and measurement of absorbance at 550 nm. FIG. 9 demonstrates that peptide CNF011.05D increases production of $NO_2$, and accordingly, production of NO in treated cells.

The induced production of NO supports the use of CNF011.05D in wound repair, for (1) cells in wounds produce NO during the proliferative phase of healing and the healing cascade (Witte and Barbul, *Am. J. Surg.* 183:406-12 (2002)); and (2) NO in wounds augments healing, for example, it increases angiogenesis in wounds, and recruits inflammatory cells into wounds that are important for healing (Zhu et. al., *J. Burn Care Res.* 29:804-14 (2008)).

Example 3

Production of Extracellular Matrix Proteins

Human fibroblasts were acquired from ear lobe skin fragments (0.5×0.5 cm) from 5 normal African-Brazilian female donors, with age ranging from 10 to 40 years old, respectively called 2/05, 3/05, 4/05, 6/05 and 8/05. The donors were submitted to excisional biopsies in a surgical environment after free voluntary consent.

Cells from the 6th subculture were placed in sterile culture plates and incubated with CNF011.05D at concentrations of 0.35 µg and 5 µg in culture medium for 4 days. The control group consisted of fibroblasts cultured under the same conditions, in which saline solution (a solvent of CNF011.05D) was added in the place of CNF011.05D.

Indirect immunofluorescence was performed using (1) Anti-fibronectin (cellular) mAb OR anti-human tenascin mAb (Sigma-USA); and (2) Alexa Fluor 488 (Molecular Probes-USA).

Production of Fibronectin

Samples tested are FBN-CN (cells treated with saline), FBN-0.35 (cells treated with CNF011.05D at 0.35 µg), and FBN-5 µg (cells treated with CNF011.05D at 5 µg).

Figure 7:
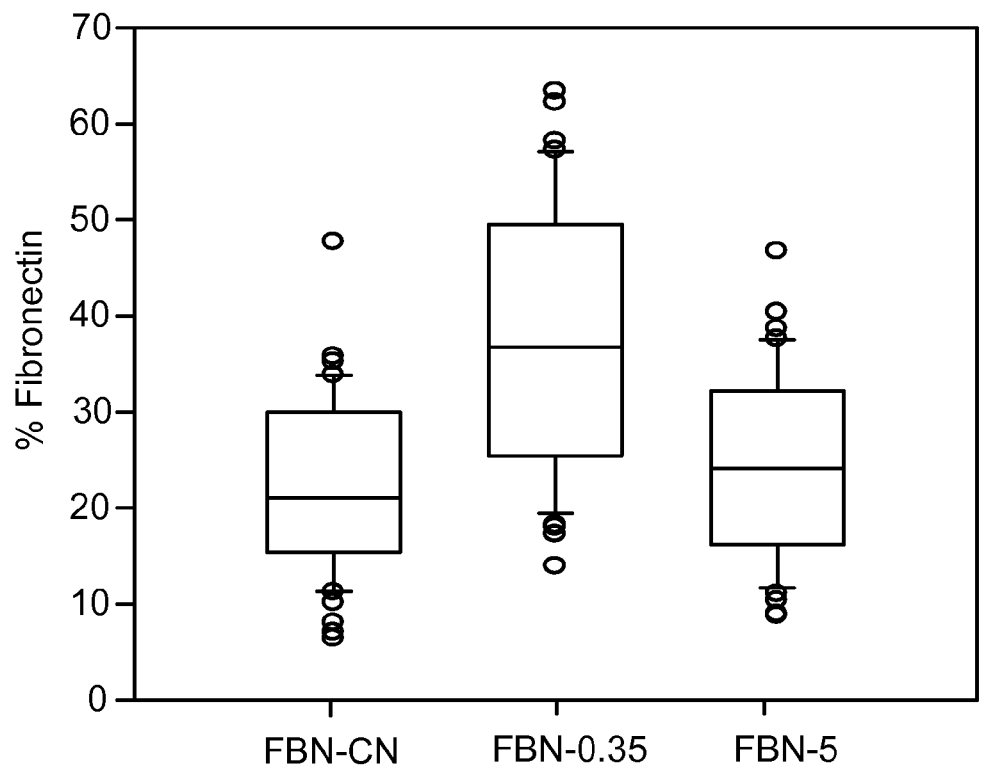
FIG. 7 is a plot illustrating the percent of fibroblasts producing fibronectin upon incubation with peptide CNF011.05D at 0.35 µg and 5 µg.

The results from indirect immunofluorscence for the production of fibronectin are illustrated in FIG. 7, and demonstrate a significant enhancement (p<0.001) in the production of fibronectin by fibroblasts cultured with CNF011.05D at 0.35 µg.

Production of Tenascin

Samples tested are CN (cells treated with saline), TN-0.35 (cells treated with CNF011.05D at 0.35 µg), and TN-5 µg (cells treated with CNF011.05D at 5 µg).

Figure 8:
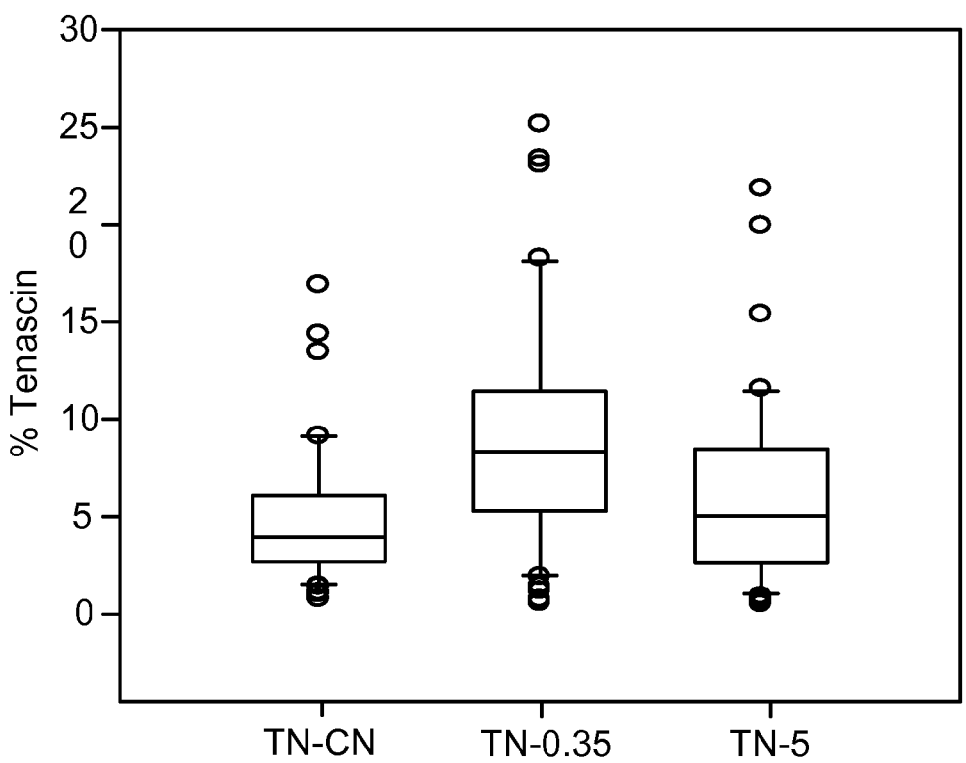
FIG. 8 is a plot illustrating the percent of fibroblasts producing tenascin upon incubation with peptide CNF011.05D at 0.35 µg and 5 µg.

Results from indirect immunofluorescence for tenascin production in FIG. 8 showed a significant difference (p<0.001) in tenascin production by fibroblasts cultured with CNF011.05D at 0.35 µg.

Production of Procollagen

Samples tested are % procol/control (cells treated with saline), % procol/0.35 (cells treated with CNF011.05D at 0.35 µg), and % procol/5 µg (cells treated with CNF011.05D at 5 µg).

Results from indirect immunofluorescence for procollagen production in FIG. 9 showed a significant difference (p<0.001) in procollagen production by fibroblasts cultured with CNF011.05D at 0.35 µg.

Example 4

Production of Collagen in the Dermis

Levels of collagen were examined after different administrations of CNF011.05D: a single subcutaneous dose, two subcutaneous doses, and four subcutaneous doses.

TABLE 2

Percent collagen in the dermis of animals after single subcutaneous dose of CNF011.05D (0.30 µg) (groups AE and BE) or saline (groups AD and BD). Values were obtained at 1, 2, or 12 weeks after final dose.

| Control Skin | | Collagen | Assessment | Number of | Single | Treated Skin | | Collagen |
|---|---|---|---|---|---|---|---|---|
| Animal | Skin | (%) | after dose | Treatments | Dose | Animal | Skin | (%) |
| G2S1AD | 2AD | 27.83 | 1 week | 1 | 0.30 | G2S1AE | 2AE | 41.20 |
| G2S1BD | 2BD | 38.07 | 1 week | 1 | 0.30 | G2S1BE | 2BE | 57.15 |
| G2S2AD | 8AD | 32.78 | 2 weeks | 1 | 0.30 | G2S2AE | 8BE | 43.78 |

TABLE 2-continued

Percent collagen in the dermis of animals after single subcutaneous dose of CNF011.05D (0.30 µg) (groups AE and BE) or saline (groups AD and BD). Values were obtained at 1, 2, or 12 weeks after final dose.

| Control Skin | | Collagen | Assessment | Number of | Single | Treated Skin | | Collagen |
|---|---|---|---|---|---|---|---|---|
| Animal | Skin | (%) | after dose | Treatments | Dose | Animal | Skin | (%) |
| G2S2BD | 8BD | 33.99 | 2 weeks | 1 | 0.30 | G2S2BE | 8AE | 39.20 |
| G2S5AD | 19AD | 28.24 | 12 weeks | 1 | 0.30 | G2S5AE | 19AE | 29.57 |
| G2S5BD | 19BD | 21.68 | 12 weeks | 1 | 0.30 | G2S5BE | 19BE | 27.22 |

TABLE 3

Percent collagen in the dermis of animals after two subcutaneous doses (0.30 µg) (groups AE and BE) or saline (groups AD and BD). Doses were given on one week apart, and values were obtained 1 week or 12 weeks after final dose.

| Control Skin | | Collagen | Assessment | Number of | Total | Treated Skin | | Collagen |
|---|---|---|---|---|---|---|---|---|
| Animal | Skin | (%) | after dose | Treatments | Dose | Animal | Skin | (%) |
| G6S2AD | 9AD | 24.27 | 2 weeks | 2 | 0.60 | G6S2AE | 9AE | 44.19 |
| G6S2BD | 9BD | 30.00 | 2 weeks | 2 | 0.60 | G6S2BE | 9BE | 37.91 |
| G6S6AD | 21AD | 24.71 | 12 weeks | 2 | 0.60 | G6S6AE | 21AE | 39.23 |
| G6S6BD | 21BD | 29.12 | 12 weeks | 2 | 0.60 | G6S6BE | 21BE | 47.33 |

TABLE 4

Percent collagen in the dermis of animals after four subcutaneous doses (0.30 µg) (groups AE and BE) or saline (groups AD and BD). Consecutive doses were given one week, and values were obtained 4 weeks after final dose.

| Control Skin | | Collagen | Assessment | Number of | | Treated Skin | | Collagen |
|---|---|---|---|---|---|---|---|---|
| Animal | Skin | (%) | after dose | Treatments | Total | Animal | Skin | (%) |
| G6S4AD | 13AD | 25.23 | 4 weeks | 4 | 1.20 | G6S4AE | 13AE | 37.60 |
| G6S4BD | 13BD | 24.42 | 4 weeks | 4 | 1.20 | G6S4BE | 13BE | 34.94 |

Example 5

Wound Healing in Rats

Size and microscopic appearance of punch wounds was assessed in rats after a single dose of CNF011.05D. The rats were Wistar rats of 6-to-8 weeks of age, which were anesthesized and operated on the dorsal side of their backs. Following clipping of hair and scrub sterilization, wounds were made in each rat using a 6 mm biopsy punch. Following wounding and drying with sterile gauze, wounds were subjected to (1) bandaging (Standard Care) or (2) application of CNF011.05D (235 nM in saline) followed by bandaging. Wounds evaluated at Days 3, 7, 14, and 21 were assessed by veterinarians and documented as to whether the wound was healing normally for the day post-wounding, and the size of the wound in $cm^2$.

TABLE 5

The size of punch wounds are shown in Table 5 at different times after surgery for 8 rats per timepoint. CNF011.05D demonstrates a faster rate of reducing wound size.

| Sample | Day 3 Size | Day 7 Size | Day 14 Size | Day 21 Size |
|---|---|---|---|---|
| Standard | 0.229 $cm^2$ | 0.093 $cm^2$ | 0.069 $cm^2$ | Scar |
| CNF011.05D | 0.200 $cm^2$ | 0.084 $cm^2$ | 0.053 $cm^2$ | Scar ** |

The timepoints at 21 days showed closed wounds and a scar. The wounds treated with CNF011.05D had scars of reduced size and color in comparison to wounds treated with Standard Care (negative control).

Example 6

Wound Healing in Pigs

Levels of granulation tissue formation—a marker of the proliferative phase of Healing (Cascade)—were assessed in punch wounds after daily administrations of CNF011.05D or positive control (Bacaplermin gel 0.01%). The wounded animals were Domestic Yorkshire Crossbred pigs of 20 weeks of age, which were anesthesized and operated on the dorsal side of their backs. Following clipping of hair and scrub sterilization, 8 full thickness wounds were made in each pig using an 8 mm biopsy punch.

Following wounding and drying with sterile gauze, the wounds were subjected to application with different treatments (see Table 5 and 6) followed by bandaging. Long-term postoperative monitoring included daily inspection of the surgical sites for 14 days. The daily inspection included cleansing of the wounds, reapplication of the same treatments—Standard Care or Positive Control or CNF011.05D (1×) or CNF011.05D (100×)—followed by rebandaging. Wounds evaluated at Days 1, 4, 7, 10, and 14 were assessed by veterinarians and documented as to whether the wound was healing normally for the day post-wounding, and the first appearance of granulation tissue filling the entire wound.

TABLE 6

Following wounding and drying with sterile gauze, (1) four wounds were subjected to bandaging (Standard Care); (2) four wounds was subjected to application of the Positive Control followed by bandaging; (3) six wounds were subjected to application of CNF011.05D (1x) (1 ml at 1.57 μg/ml in saline) followed by bandaging; and (4) six wounds were subjected to application of CNF011.05D (1 ml at 157 μg/ml in saline) (100X) followed by bandaging.

Wounds with the first appearance of granulation tissue filling the entire wound are indicated in the Yes row of Table 6. CNF011.05D (1x) and CNF011.05D (100x) demonstrate faster rates of complete filing than the Standard Care (negative control).

| Sample | Granulation Tissue Filling | Day 1 | Day 5 | Day 7 | Day 10 | Day 14 |
|---|---|---|---|---|---|---|
| Standard | Yes | — | 1 | 2 | 3 | 3 |
|  | No | 4 | 3 | 2 | 1 | 1 |
| Positive | Yes | — | 2 | 3 | 3 | 4 |
|  | No | 4 | 1 | 1 | 1 | — |
| CNF011.05D 1x | Yes | — | 3 | 4 | 6 | 6 |
|  | No | 6 | 3 | 2 | — | — |
| CNF011.05D 100x | Yes | — | — | 1 | 6 | 6 |
|  | No | 6 | 6 | 5 | — | — |

TABLE 7

Following wounding and drying with sterile gauze, (1) two wounds were subjected to application of CNF011.05D (1x) (1 ml ointment at 1.57 μg/ml in Hydroxyethyl cellulose/Glycerin (20%/80%) followed by bandaging; and (2) two wounds were subjected to application of CNF011.05D (100x) (1 ml ointment at 157 μg/ml in Hydroxyethyl cellulose/Glycerin (20%/80%) followed by bandaging.

Wounds with the first appearance of granulation tissue filling the entire wound are indicated in the Yes row of Table 7. CNF011.05D in ointment demonstrates faster rates of complete filing than the Standard Care (negative control) or CNF011.05D in saline (Table 6).

| Sample | Granulation Tissue Filling | Day 1 | Day 5 | Day 7 | Day 10 | Day 14 |
|---|---|---|---|---|---|---|
| CNF011.05D 1x | Yes | — | 2 | 2 | 2 | 2 |
|  | No | 2 | — | — | — | — |
| CNF011.05D 100x | Yes | — | 2 | 2 | 2 | 2 |
|  | No | 2 | — | — | — | — |

What is claimed is:

1. An isolated peptide of 17 amino acids or less that comprises the amino acid sequence: YAIGYSCKDYK (SEQ ID NO: 1), wherein the peptide is capable of stimulating production of at least one of fibronectin, tenascin, or procollagen in fibroblast cells or collagen in dermis.

2. An isolated peptide of 35 amino acids or less that comprises the amino acid sequence: APLWILSTDYDNYAIGY-SCKDYK (SEQ ID NO:5), wherein the peptide is capable of stimulating production of at least one of fibronectin, tenascin, or procollagen in fibroblast cells or collagen in dermis.

3. An isolated peptide consisting of the amino acid sequence: YAIGYSCKDYK (SEQ ID NO:1).

4. An isolated peptide consisting of the amino acid sequence: APLWILSTDYAIGYSCKDYK (SEQ ID NO:5).

5. A pharmaceutical composition comprising the peptide of any one of claim 1, 2, 3, or 4 and a pharmaceutically acceptable carrier.

6. The pharmaceutical composition of claim 5, wherein the pharmaceutically acceptable carrier is a water-based diluent.

7. The pharmaceutical composition of claim 5, wherein the composition is in the form of a liquid or an ointment.

8. The pharmaceutical composition of claim 5, wherein the composition further comprises a wound healing agent.

9. The pharmaceutical composition of claim 5, wherein the composition is in the form of a liquid solution, dispersion, suspension, tablet, pill, powder, suppository, gel, or ointment.

10. The pharmaceutical composition of claim 5, wherein the composition is in the form of a cream, gel, lotion, or salve.

* * * * *

UNITED STATES PATENT AND TRADEMARK OFFICE
CERTIFICATE OF CORRECTION

PATENT NO. : 8,883,740 B2  
APPLICATION NO. : 12/863922  
DATED : November 11, 2014  
INVENTOR(S) : Janaina de Souza Ventura et al.

It is certified that error appears in the above-identified patent and that said Letters Patent is hereby corrected as shown below:

Title Page, item (73), column 1 (Assignees), line 2, delete "Amparoa" and insert -- Amparo a --;

Title Page, item (56), column 2 (Other Publications), line 1, delete "oblique" and insert -- obliqua --;

In the Specification

In column 1, line 5, after "U.S.C." insert -- § --; and

In the Claims

In column 18, line 49, in Claim 5, delete "claim" and insert -- claims --.

Signed and Sealed this
Seventeenth Day of March, 2015

Michelle K. Lee
*Director of the United States Patent and Trademark Office*